United States Patent
Spargias

(10) Patent No.: US 10,531,951 B2
(45) Date of Patent: Jan. 14, 2020

(54) TRANSCATHETER PROSTHETIC HEART VALVE AND DELIVERY SYSTEM

(71) Applicant: Edwards Lifesciences Corporation, Irvine, CA (US)

(72) Inventor: Konstantinos Spargias, Athens (GR)

(73) Assignee: Edwards Lifesciences Corporation, Irvine, CA (US)

( * ) Notice: Subject to any disclaimer, the term of this patent is extended or adjusted under 35 U.S.C. 154(b) by 98 days.

(21) Appl. No.: 15/526,810

(22) PCT Filed: Nov. 26, 2015

(86) PCT No.: PCT/EP2015/077856
§ 371 (c)(1),
(2) Date: May 15, 2017

(87) PCT Pub. No.: WO2016/083551
PCT Pub. Date: Jun. 2, 2016

(65) Prior Publication Data
US 2017/0333186 A1 Nov. 23, 2017

(30) Foreign Application Priority Data

Nov. 26, 2014 (GR) .............................. 20140100595

(51) Int. Cl.
*A61F 2/24* (2006.01)
(52) U.S. Cl.
CPC .......... *A61F 2/2418* (2013.01); *A61F 2/2436* (2013.01); *A61F 2210/0014* (2013.01); *A61F 2220/0008* (2013.01); *A61F 2220/0016* (2013.01); *A61F 2250/0063* (2013.01)

(58) Field of Classification Search
CPC ........ A61F 2/24; A61F 2/2418; A61F 2/2436; A61F 220/0016; A61F 220/0008
See application file for complete search history.

(56) References Cited

U.S. PATENT DOCUMENTS

| 8,062,355 B2 | 11/2011 | Figulla et al. |
| 2005/0137702 A1 | 6/2005 | Haug et al. |
| 2010/0312333 A1 | 12/2010 | Navia et al. |

(Continued)

FOREIGN PATENT DOCUMENTS

| CN | 201076530 Y | 6/2008 |
| CN | 103997990 A | 8/2014 |

(Continued)

OTHER PUBLICATIONS

Chinese Office Action issued in corresponding CN Application No. 201580063228.8 dated Jan. 24, 2018 (15 pages).

(Continued)

*Primary Examiner* — Vi X Nguyen

(57) ABSTRACT

A prosthetic heart valve for an endoprosthesis used in the treatment of a stenotic heart valve and/or a heart valve insufficiency. The prosthetic heart valve comprises a plurality of leaflets (3,4,5) which are able to switch between their open and close position in response to the blood flow through the heart. The leaflets are attached into a collapsible wire valve frame involving a stent part (1) and a wire mesh part (2) that complement each other in many ways. The prosthetic valve comprises additional elements (6) for its correct positioning and stabilization.

12 Claims, 16 Drawing Sheets

(56) References Cited

U.S. PATENT DOCUMENTS

2013/0310928 A1* 11/2013 Morriss ................ A61F 2/2418
623/2.12
2014/0222136 A1  8/2014 Geist et al.

FOREIGN PATENT DOCUMENTS

| EP | 1942834 B1 | 1/2013 |
| WO | 2012177942 A2 | 12/2012 |
| WO | 2013103612 A1 | 7/2013 |
| WO | 2014121275 A1 | 8/2014 |

OTHER PUBLICATIONS

International Search Report for International Application No. PCT/EP2015/077856 dated May 12, 2016.
Notification of the Second Office Action issued by the State Intellectual Property Office of the People's Republic of China dated Sep. 29, 2018 in corresponding CN Patent Application No. 201580063228.8, with English translation.
Communication Pursuant to Article 94(3) EPC issued by the European Patent Office dated Jan. 2, 2019 in corresponding European Patent Application No. 15830778.5.

* cited by examiner

TRANSCATHETER PROSTHETIC HEART VALVE AND DELIVERY SYSTEM

CROSS REFERENCE TO RELATED APPLICATIONS

This application is a U.S. National Stage entry of International Application No. PCT/EP2015/077856, filed on Nov. 26, 2015, which claims priority to Greek Patent Application No. 20140100595 filed on Nov. 26, 2014, the disclosures of each of which are hereby incorporated by reference herein in their entirety.

FIELD OF THE INVENTION

The invention generally relates to devices for cardiovascular treatment. More specifically, the invention generally relates to devices for percutaneous heart valve replacement/implantation.

BACKGROUND OF THE INVENTION

Valvular heart disease is common and involves considerable mortality and morbidity. Surgical replacement of the failing valve is the treatment of choice when the disease progresses and certain criteria are fulfilled. However, it is not uncommon patients fulfilling the criteria for this treatment to be rejected due to a perceived unacceptably high surgical risk for a variety of reasons such as advanced age and comorbidities. For some it is their decision to deny this treatment. These factors drove the development of prosthetic heart valve devices that can be implanted percutaneously with guiding catheters. Many such devices for the treatment of aortic valve stenosis have gained regulatory approvals and are already successfully and widely used offering clinical and survival benefits in many patients. Recently, we have seen the first device gaining regulatory approval for the percutaneous treatment of aortic valve insufficiency.

Aortic and mitral valve disease (stenosis and/or insufficiency) are equally common but despite the success in developing percutaneous prosthetic valves for the aortic valve, developing a device for percutaneously replacing the mitral valve have been challenging and problematic. The main reason is the much more complex and uneven anatomy of the mitral valve.

Apparently, the development of such a device for the percutaneous replacement of the mitral valve would be of great benefit for many patients.

This invention provides numerous alternative solutions to overcome these problems and develop a successful percutaneously delivered prosthetic mitral valve. Some of the solutions described could be used for similar prosthetic devices for implantation in other heart valves.

SUMMARY OF THE INVENTION

The invention relates to a prosthetic heart valve for an endoprosthesis used in the treatment of a stenotic heart valve and/or a heart valve insufficiency. The prosthetic heart valve comprises a plurality of leaflets, which consist of a natural and/or synthetic material and are being able to switch between their open and close position in response to the blood flow through the heart. The leaflets are attached into a collapsible wire valve frame involving a stent part and a wire mesh part that complement each other in many ways. The frame has a body that defines a lumen to its inside. The exterior portion of the frame has features that serve for its conformation and stabilization/anchoring in the anatomic structures it contacts. When the endoprosthesis apparatus is expanded within the intended failing native heart valve it replaces it and resumes its function.

The endoprosthesis is contained in a sheathed capsule and is inserted into the body and advanced to the intended location with a delivery system for percutaneously deploying a prosthetic heart valve. This system apart from the sheathed capsule includes an inner shaft assembly, and a handle maintaining control knobs that enable independent movement of the various parts of the sheathed capsule and the endoprosthesis. The handle functions allow for gradual release and deployment of the endoprosthesis, but also can recapture the endoprosthesis and safely remove it out of the body even after its complete deployment to its full functional status.

DETAILED DESCRIPTION OF THE INVENTION

Transcatheter Mitral Valve

Figure 1:
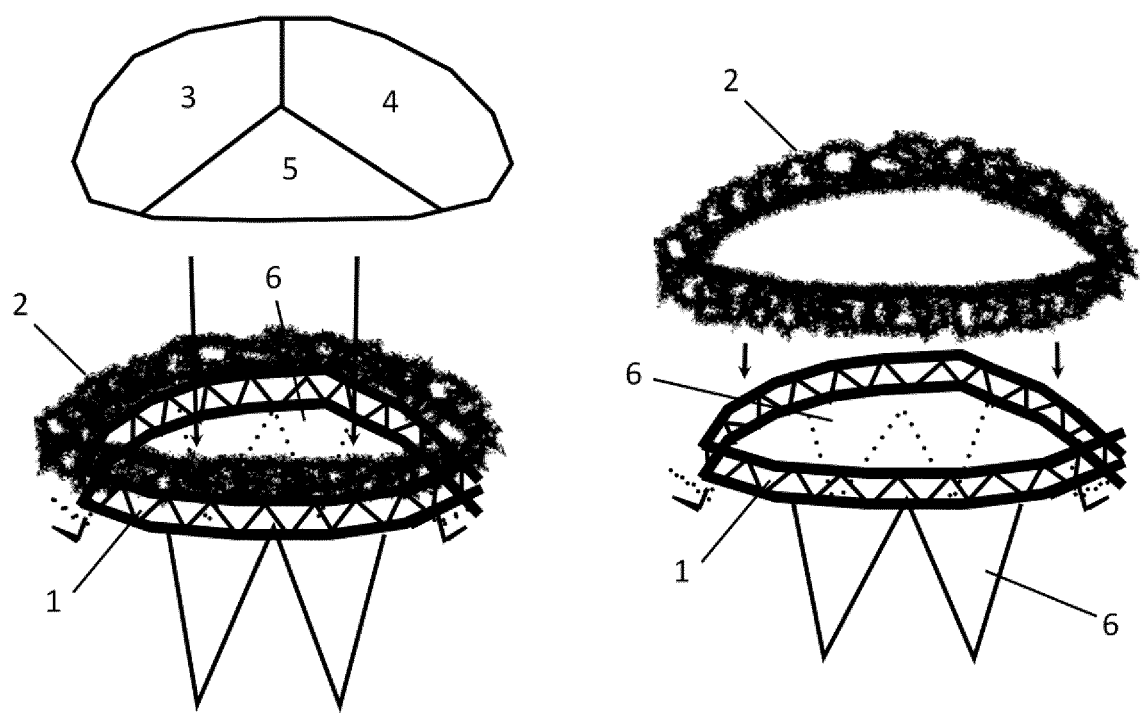
FIG. 1 shows a first embodiment of a prosthetic valve according to the present invention.

This prosthetic heart valve and its delivery system are intended for use in the treatment of mitral valve insufficiency and/or mitral valve stenosis. The delivery method is retrograde (the approach of the diseased mitral valve is achieved from within the left ventricle-transapical access and against the flow of the blood) or antegrade (the approach of the diseased mitral valve is achieved from within the left atrium after direct surgical approach or transeptal puncture and along with the flow of the blood), with the use of specifically designed for each access delivery systems. The endoprosthesis comprises of a plurality of leaflets attached to a collapsible wire frame. This frame integrates a stent part and a braided and/or flat wire mesh part that complement each other in many ways. The combination of these two different resources in building the frame of the transcatheter valves described in this invention is very important and it is believed to solve many of the problems encountered to date for the development of a successful percutaneous prosthetic mitral valve. The stent part towards its ventricular end and the wire mesh part towards its atrial end. The wire mesh surrounds the stent at the atrial end and forms a body around the stent extending beyond the atrial end. According to certain embodiments of the present invention, the wire mesh extends also longitudinally towards the ventricular end of the stent forming again a body around the stent. There are limitless combinations of the relative length proportions of the endoprosthesis these parts may occupy, and they may overlap. It can have several standardized shapes and sizes. It can even be custom made based on measurements from the patient's anatomy obtained by medical imaging.

The outer parts of the wire mesh towards the atrium may be braided or flat. The rest of the wire mesh is braided. The stent part that will cover at least the annulus level has a sealing skirt from suitable material. The stent part may be cylindrical or conical (and may have a flaring towards the ventricle in order to withstand the excessive systolic forces exerted on the device with every heart beat). The wire mesh part can incorporate a fabric or other sealing material to make it instantly impermeable.

The stent part may be made of collapsible nitinol, stainless steel or other material and can self-expand. The wire mesh may be made of collapsible nitinol, stainless steel or other material and can self-expand. The advantages of the stent component is that it has maximal radial force and thus can appose and stabilize the frame optimally in areas of the mitral valve this is needed (such as the annulus area). It also provides the areas at which the prosthetic valve leaflets are attached and other structures described later. The wire mesh on the other hand, can better conform and adapt to areas of uneven and unpredictable anatomy and offer optimal sealing of unwanted blood flow by doing so. The shutting of unwanted blood flow can be instant when fabric or other components are incorporated into or on the mesh. The flat wire mesh can expand to larger diameters and reach longer where needed without occupying large volumes. The braided wire mesh may expand less but it self-adjusts perfectly to fill in restrained spaces (such as spaces between the mitral valve annulus and the stent part of the frame) and to assume the shape of the anatomy it apposes to (such as the mitral valve annulus).

Figure 2:
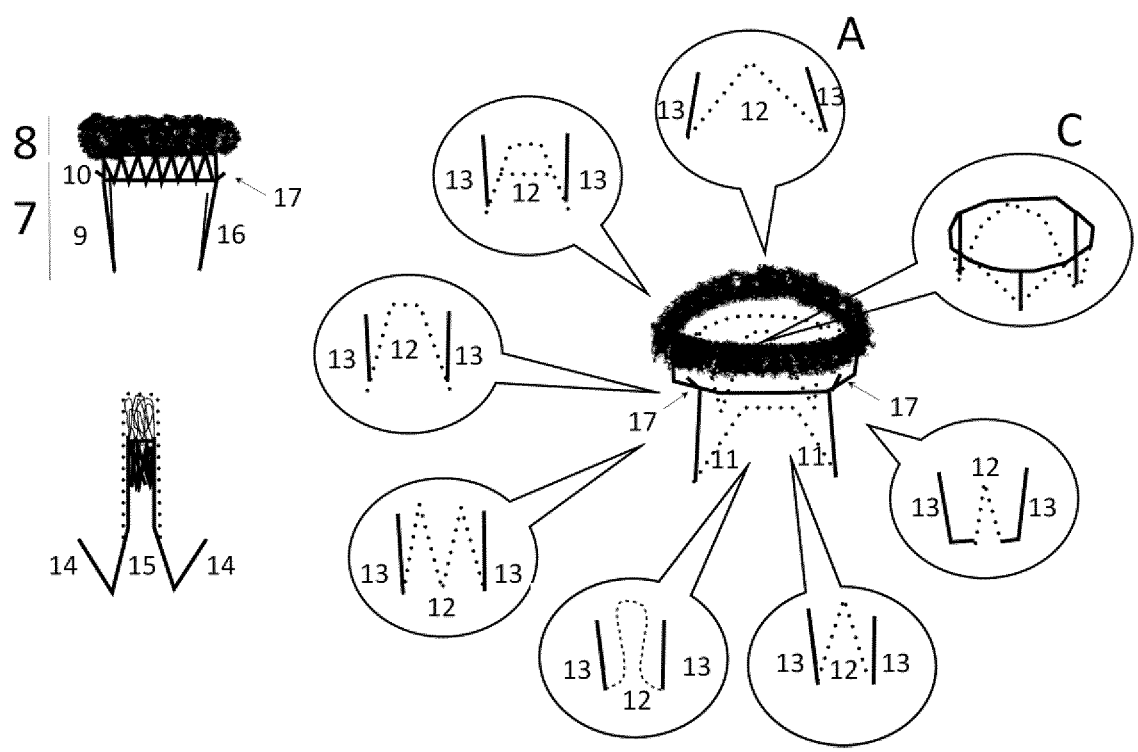
FIG. 2 shows a further embodiment of a prosthetic valve according to the present invention.

The endoprosthesis frame apposes to the intended area and its anatomically designed shape together with its radial strength and its other supporting features allow it to steadily fix. In addition, the frame has particular features on its outer surface that allow deploying the endoprosthesis at the anatomically appropriate area. The frame also allows for degrees of auto-adjustment towards the anatomically appropriate area/plane. Besides the integration of a stent and a wire mesh to form the frame of the endoprosthesis, the second most important feature in the invented solutions presented in the following sections is the provision of particular components of the stent to guide and retain the device to the anatomically correct deployment position by tracking these components behind the native mitral valve leaflets and capturing them wide-open (FIG. 2, 9). These components are referred to as capturing elements. According to a preferred embodiment of the present invention, the capturing elements comprise a part that extends radially beyond the body of the wire mesh which surrounds the stent.

The valve leaflets can consist of a natural and/or synthetic material and are being able to switch between their open and close position in response to the blood flow through the mitral valve. Their fixed sides are seamed or attached with other means at the wire frame of the endoprosthesis (such as the stent ring end and the interior native valve leaflet enveloping elements). They start to function when the wire mesh part of the endoprosthesis is released.

The delivery catheter comprises a distal capsule that contains the endoprosthesis at its compressed state and the catheter shaft assembly that extends from within the capsule to the outer system handle. The handle maintains control knobs and/or dials and/or buttons that are connected to layers of the shaft assembly that on their other end within the capsule function to gradually open the capsule and uncover the endoprosthesis. This causes the uncovered parts of the latter to assume their default-uncompressed state and shape, allowing the inner lumen of the frame to form and the valve leaflets to commence function propelled by the blood flow. The handle also maintains functions that allow through shaft layers and or other components to resheath and remove the endoprosthesis even after full delivery and function is achieved.

The device allows for complete atraumatic re-capture/research and removal of the endoprosthesis even after its full deployment and assumption of its function.

DETAILED DESCRIPTION OF THE EMBODIMENTS

Embodiment 1

FIG. 1 shows a first embodiment of a prosthetic mitral valve according to the present invention comprising a stent (1) and a wire mesh (2) surrounding the stent at the atrial end and forming a body around the stent (2) which extends beyond the atrial end. The stent comprises internally three valve leaflets (3,4,5). Furthermore, the stent forms at its ventricular end a pair of capturing elements (6) which capture the native leaflets thus providing positioning guidance and anchoring/retention.

Embodiment 2

The endoprosthesis (FIG. 2) comprises of a plurality of leaflets, which consist of a natural and/or synthetic material and are being able to switch between their open and close position in response to the blood flow through the heart. The leaflets are attached into a collapsible wire valve frame that includes a stent (7) and a wire mesh (8). The frame has a body that defines a lumen to its inside. The exterior portion of the frame has features that serve for its conformation and stabilization/anchoring in the anatomic structures it contacts. When the endoprosthesis apparatus is expanded within the intended failing native heart valve it replaces it and resumes its function. The frame of the endoprosthesis includes a stent and a wire mesh. All these are also described in the embodiment 1.

The stent part of the endoprosthesis includes a crown (9), and a ring (10). The crown includes capturing elements for each of the native valve leaflets (11). Each such element has an exterior (12) and an interior part (13) for enveloping/capturing/clipping the respective native valve leaflet. The first component of the stent that expands within the left ventricle is the part of the crown that has at least two external wings/hooks/clipping elements (14), also shown in FIG. 3A, 3B, which are the first to appear when the ventricular part of the capsule starts to open towards the apex of the ventricle. Once released, they are fully expanded. Their expansion ("opening") is achieved by the default design of the frame as they exit the sheath and possibly from special features at their articulation to the rest of the frame (such as thicker areas of the struts close to the articulation that push away the external elements when released, but as the frame opens these areas do not overlap anymore and the external elements come close again to their internal counterparts to clip the leaflets).

These external elements when released are aligned using continuous real-time imaging modalities, such as transesophageal echocardiography, to extend behind (outside) each of the two native mitral valve leaflets. At the same time the tips of the interior enveloping/capturing/clipping elements start to flare (15) when the ventricular side of the capsule opens to fully release their outer counterparts. Once this is achieved the entire system is moved so that the tips of the exterior wings/hooks/clipping elements approach and contact the mitral valve annulus at its ventricular side. It is expected that when this occurs the operator will experience resistance providing tactile feedback for the correct positioning. During this initial phase the native mitral valve function is uninterrupted. The exterior elements by sitting behind the leaflets and reaching deep into the annulus create an anchoring of the entire frame on the ventricular side of the mitral annulus.

Then, and while exerting a steady force to keep the external wings/hooks/clipping parts at or as close as possible to the ventricular side of the mitral annulus, the atrial side of the capsule opens releasing the rest of the endoprosthesis frame.

The first to be released next is the part of the stent crown that holds the bases of the internal enveloping/capturing/clipping elements. These expand towards their external counterparts and capture/envelop/clip the native valve leaflets locking them into a wide-open position by doing so. By pairing these hooking components on either side of the native valve leaflets these are engulfed/enveloped/clipped in between them and as the frame keeps expanding they are locked in this position. The interior pairing constituents (13) have sufficient length to capture at least the tips of the native leaflets before they join the stent ring. They may also be made to have a progressively greater default expansion towards the annulus (16) than their exterior counterparts, and by doing so they fix the native valve leaflets actively inside (essentially by clipping them). The pairing components can have a range of shapes that pinch the native leaflets in between (12,13). Furthermore, the capture elements of the anterior and posterior native valve leaflets may differ in shape to match the different anatomy of these leaflets. For example, the exterior elements of the anterior leaflet may be wider and longer than their interior counterparts and have a reversed M shape so that their two bases are seated closer to the fibrous trigones on both sides of the anterior leaflets (FIG. 2A).

After the stent crown is released and the native valve leaflets are locked wide open in it, the ring of the stent is released. The stent ring has a fabric skirt layer attached for sealing the areas of the annulus it apposes to from unwanted blood flow. The shape of the ring may be rather oval and in any case resembling and conforming optimally with the shape of the mitral valve annulus. Externally it may have anchoring elements such as hooks, barbs, spikes, indentations or similar (17) to secure on the annulus as it apposes against it, and provide additional stabilization of the endoprosthesis at the annulus on this occasion. These anchoring features are mainly found towards the perimeter of the stent that apposes to the commissural areas of the annulus. Maximal radial strength is given at the larger diameter of the stent. The radial strength of the stent arc that apposes the annulus at the root of the anterior leaflet is calculated so that it does not push the leaflet into the outflow tract of the left ventricle and cause obstruction. For the same reason, the clipping mechanism of the anterior leaflet when fully expanded may have an incline away from the outflow tract.

In the interior part of the stent ring there are elements for passively attaching the endoprosthesis on its delivery catheter pins during the crimping process. This passive attachment offers stabilization of the endoprosthesis on its delivery catheter while the capsule components move to release various parts of it, till of course the capsule uncovers the area of the stent ring that sits on the catheter pins and releases it.

The prosthetic valve leaflets are attached to the stent ring and the interior enveloping elements of the stent crown but can also be attached at other purposely-devoted posts of the stent (FIG. 2C).

Lastly, the wire mesh part of the endoprosthesis (8) is released by continued opening of the atrial side of the capsule (FIG. 3C, 3D). This consists of a rather oval shaped (that in any case resembles the anatomy of the annulus) thin wire mesh that can incorporate a fabric or other material to make it instantly impermeable. It is attached and is the continuation of the most atrial side of the stent. When released, it expands from the native valve annulus overlapping with the stent towards the surrounding atrial walls. It has sufficient length to extent enough into the atrial side of the mitral valve annulus. By doing so stabilizes the endoprosthesis at the atrial level of the annulus and allows auto-adjustment of the entire endoprosthesis. It has a progressively larger default diameter than the atrial side of the stent, and it may be made to have a tendency to revert backwards and appose actively to the atrial wall on the atrial side of the annulus and above it offering superior sealing from paravalvular insufficiency and improving the stabilization of the entire frame. The length of the wire mesh ring can differ locally to conform best to the anatomy it apposes to. The entire mesh wire can be braided. Alternatively, the most exterior parts of the wire mesh that are away from the annulus can be made of flat mesh, while as it comes closer to the annulus it becomes braided.

In summary, all segments offer the stabilizing mechanism of this endoprosthesis. The stent crown of the frame contains the paired elements that actively capture, envelope and lock wide open the two native valve leaflets. In addition, the bases of the exterior elements are behind the native leaflets and are immobilized by the ventricular side of the annulus. This latter segment offers also tactile feedback for the correct positioning of the endoprosthesis.

The stent ring expands and apposes the native valve annulus and has also special features for anchoring on it. Finally, the wire mesh offers stabilization at the level of the annulus and towards the atrial side and locks the endoprosthesis at its final position, offering at the same time room for self-adjustment and self-alignment.

The release of this endoprosthesis starts from the ventricle and ends in the left atrium.

The endoprosthesis can have several standardized shapes and sizes. It can even be custom made based on measurements from the patient's anatomy obtained by medical imaging.

The resheath/recapture/removal capability of the endoprosthesis, even after complete deployment, is described in the delivery catheter section.

Embodiment 3

Figure 4:
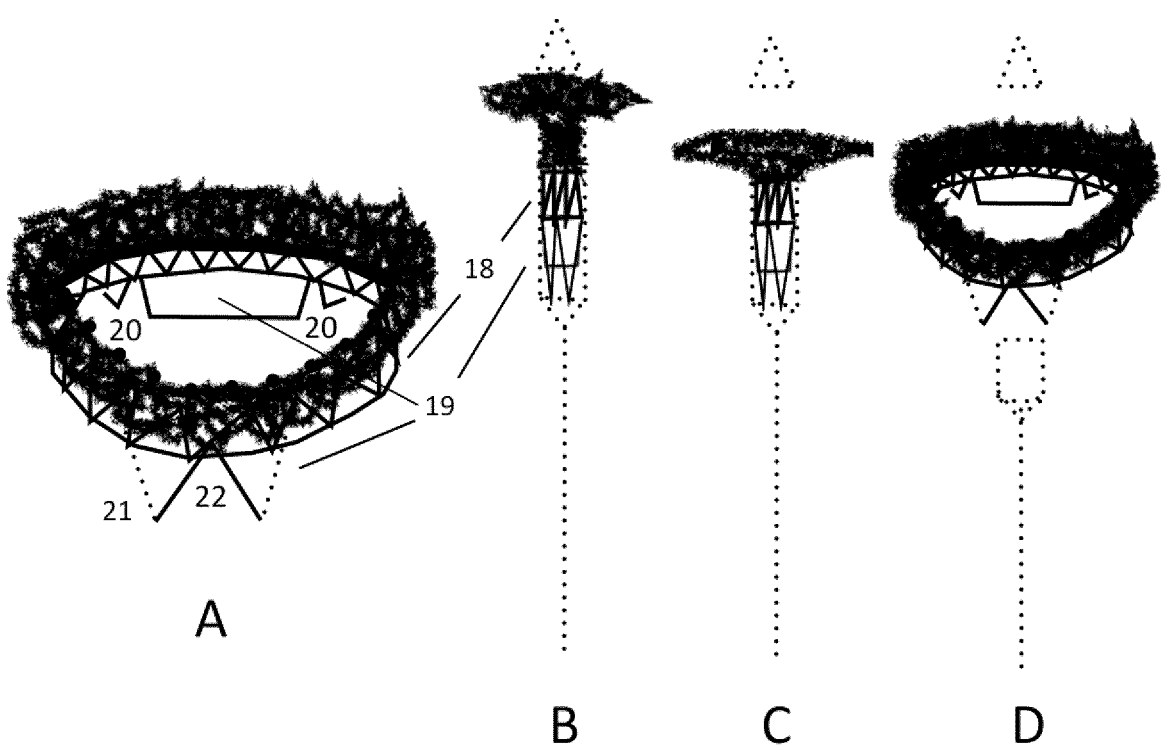
FIG. 4 shows another embodiment of a prosthetic valve according to the present invention.

Another version (FIG. 4A) of the described in the embodiment 2 endoprosthesis can be deployed in the opposite way, starting from the atrial side (FIG. 4B, 4C, 4D). First, the wire mesh is gradually released within the left atrium (FIG. 4B, 4C). The valve then is pulled downward till the wire mesh seats firmly at the floor of the atrium. Then the stent ring (18) is released followed by its crown (19) that contains a plurality of anchoring structures (hooks, barbs, spikes, indentations or similar) (20) extending into the ventricular side of the annulus. Two of them may be seated and capture the fibrous trigones on both sides of the anterior leaflet and hold this leaflet wide-open. Another component of the crown may extend in the middle part of the posterior leaflet (21). This is longer and therefore the last to be completely released from the delivery system. Its final part folds completely backwards (22) towards the ventricular side of the annulus to capture the posterior leaflet.

The elements for passively attaching of this endoprosthesis on its delivery catheter pins during the crimping process are at the most ventricular tips of the stent crown. This is the part of the endoprosthesis released last. This passive attachment offers steadiness of the endoprosthesis on its delivery catheter while the capsule components move to release various parts of it, till of course the capsule uncovers this final part.

The endoprosthesis can have several standardized shapes and sizes. It can even be custom made based on measurements from the patient's anatomy obtained by medical imaging. The prosthetic valve leaflets are attached to the stent ring and the interior enveloping elements of the stent crown but can also be attached at other areas of the wire frame.

Embodiments 4 a,b

Figure 5:
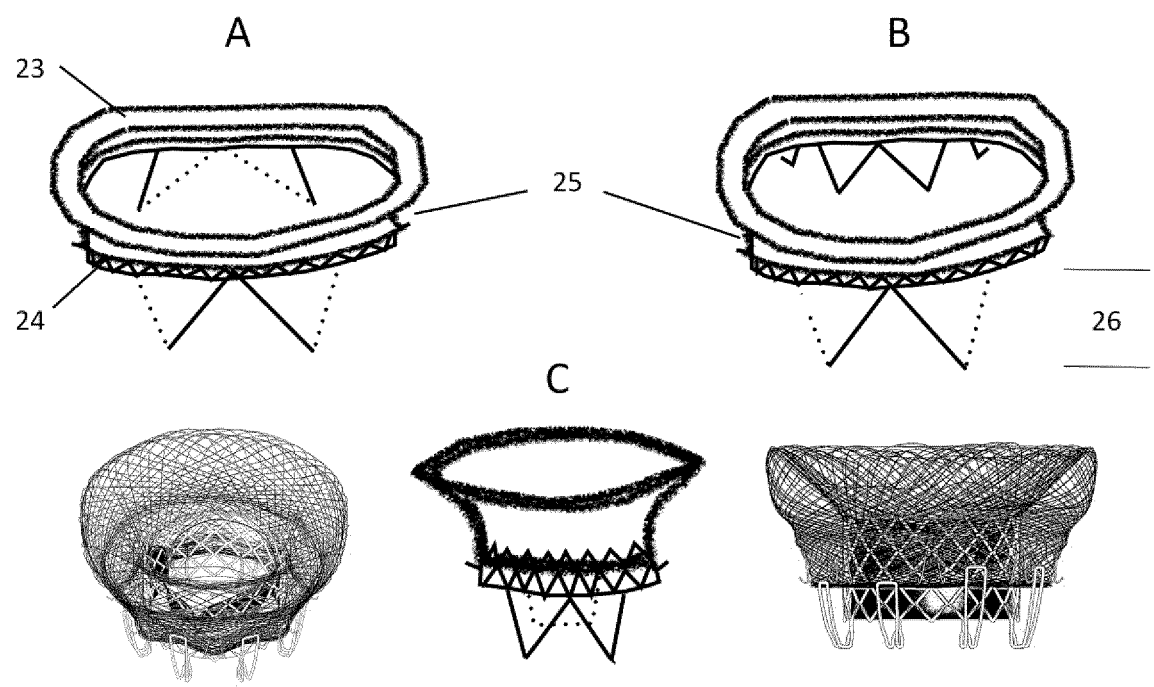
FIG. 5 shows another embodiment of a prosthetic valve according to the present invention.

Another version of either of the two previous embodiments (2 and 3) can have a more dominant wire mesh part that alone or with a degree of overlap with the stent part apposes at the annulus and succeeds the stabilization of this endoprosthesis (FIG. 5). In the previous two versions it was mainly the stent ring of the frame to be apposed and seated at the annulus level. In this version the wire mesh (23) occupies a larger length of the frame of the endoprosthesis and allows it to well reach and appose in the annulus. The stent part (24) is mostly below the annulus (FIG. 5A, 5B) but may also reach the level of the annulus and overlap internally the wire mesh (FIG. 5C).

The wire mesh of this endoprosthesis covers from just below the annulus, then covers it and extends at the surrounding atrial walls. It has a trench or channel or concavity at its outer perimeter (25) that has the shape of the annulus and slightly oversizes it, so that by expanding on the annulus sits on its both sides fixing perfectly and steadily the endoprosthesis.

The stent part in this case, connects to the wire mesh below the annulus and it is shorter. Alternatively, it may have a component to surround the wire mesh away from its outer perimeter (internally) at the level of the annulus and provide additional radial force to it (FIG. 5C). Then it has a crown part extending towards the left ventricle (26) with elements to hold or capture the native valve leaflets wide open. The stent crown can be similar to embodiment 2, and in this case the ventricular part of the endoprosthesis is first deployed allowing for capturing the native valve leaflets, self-positioning below the annulus and anchoring and stabilization at the ventricular side. Then the rest of the stent and the wire mesh are deployed (embodiment 4a) (FIG. 5A).

The stent crown can also be similar to embodiment 3, and in this case the atrial part of the endoprosthesis is first deployed and pulled downward till the wire mesh seats firmly at the floor of the atrium. Then the rest of the wire mesh is deployed surrounding the annulus and finally the stent parts that hold or capture the native valve leaflets wide-open and offer additional anchoring and stabilization at the ventricular side (embodiment 4b) (FIG. 5B).

The wire mesh incorporates a fabric or other material to make it instantly impermeable and may have a fabric skirt at the level of the annulus for better sealing. The endoprosthesis can have several standardized shapes and sizes. It can even be custom made based on measurements from the patient's anatomy obtained by medical imaging.

The prosthetic valve leaflets are attached to the wire frame of the endoprosthesis at the stent part.

Embodiment 5

Figure 6:
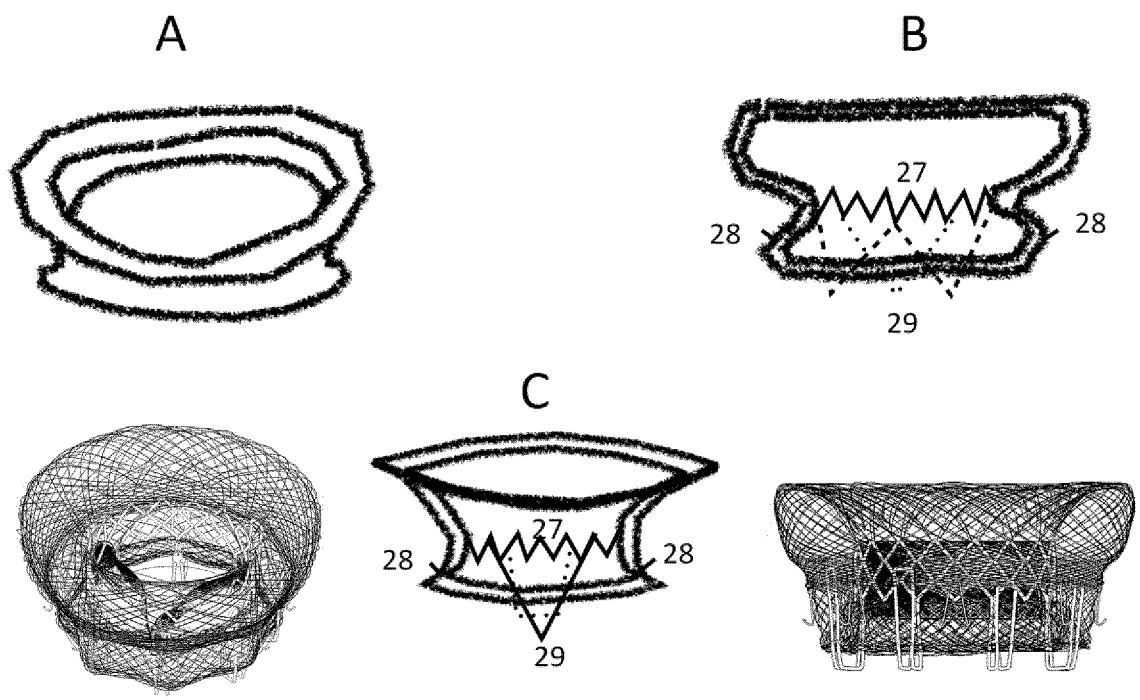
FIG. 6 shows another embodiment of a prosthetic valve according to the present invention.

This version is similar to the previous embodiment 4, but the frame of this endoprosthesis is entirely formed by the wire mesh (FIG. 6).

The atrial side is first released within the left atrium. The valve then is pulled downward till the wire mesh seats firmly at the floor of the atrium. By doing so stabilizes the endoprosthesis at the atrial level of the annulus and allows auto-adjustment of the entire endoprosthesis. It has a progressively larger default diameter at its atrial side, and it may be made to have a tendency to revert backwards and appose actively to the atrial wall on the atrial side of the annulus and above it offering superior sealing from paravalvular insufficiency and improving the stabilization of the entire frame. The dimensions of the wire mesh can differ locally to conform best to the anatomy it apposes to. The entire mesh wire can be braided. Alternatively, the most exterior parts of the wire mesh that are away from the annulus can be made of flat mesh, while as it comes closer to the annulus it becomes braided. The wire mesh incorporates a fabric or other material to make it instantly impermeable. It can also have a fabric skirt at the level of the annulus for better sealing.

Then by keeping the opened atrial part on the floor of the atrium the part that apposes at the annulus is released. This has a trench or channel or concavity at its outer perimeter that has the shape of the annulus and slightly oversizes it, so that by expanding on the annulus it sits on its both sides fixing perfectly and steadily the endoprosthesis.

The wire mesh extends more into the surrounding atrial walls than in the ventricular side of the annulus (FIG. 6A). The shape and dimensions of the atrial and ventricular parts of the mesh are such to appose comfortably at their intended locations.

This endoprosthesis wire mesh frame may have one or more of the additional components: A. A collapsible wire component, such a short stent, to surround the wire mesh internally at the level of the annulus and to provide additional radial force to it at that level (27). B. Stand-alone or connected wire elements (hooks, barbs, spikes, indentations or similar) at the outer ventricular surface of the frame for anchoring below the annulus (28). C. Particular wire posts and elements for attachment of the prosthetic leaflets and for holding the native valve leaflets wide open (29).

The wire mesh incorporates a fabric or other material to make it instantly impermeable and may have a fabric skirt at the level of the annulus for better sealing. The endoprosthesis can have several standardized shapes and sizes. It can even be custom made based on measurements from the patient's anatomy obtained by medical imaging.

The prosthetic valve leaflets are attached to the wire frame of the endoprosthesis. This endoprosthesis can be deployed either from its atrial or its ventricular side.

Embodiment 6

Figure 7:
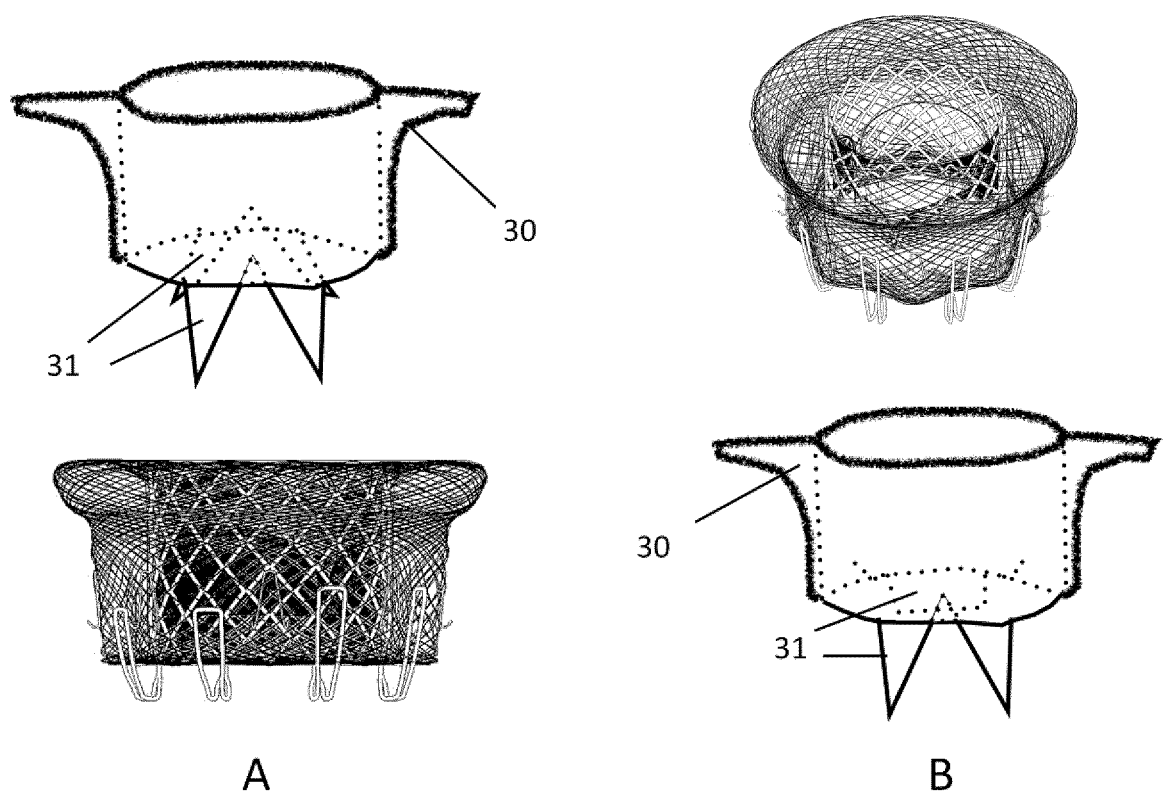
FIG. 7 shows another embodiment of a prosthetic valve according to the present invention.

This embodiment describes an endoprosthesis, which is a version of either the embodiments 2-4 endoprosthesis. The main feature of this version that makes it distinct from those embodiments is that the stent part of the endoprosthesis frame is dominant and occupies the majority or the entire length of the frame, with the wire mesh part being exterior to it forming a body around it (FIG. 7A). The lumen of the endoprosthesis is therefore defined completely by the stent, which is fully surrounded by the wire mesh.

The wire mesh (30) default shape and dimensions are to out-expand the mitral valve annulus towards the atrium to allow the seating, sealing and stabilization of the endoprosthesis at its atrial side. Then the wire mesh continues as a band surrounding the stent at the annulus area and may reach just below it. This part of the wire mesh seals the endoprosthesis at the annular level. It allows the stent to appose within it and compresses on the surrounding tissues offering an optimal adaptation and stabilization at this level.

The dominant stent part in this embodiment takes advantage of the greater radial strength the stent provides to the entire frame and it allows for the formation of a uniform and assured lumien throughout the frame. The skirted stent reaches below the annulus but is short of the tips of the leaflets and its surrounding wire mesh seals any anatomical asymmetries.

The ventricular end of the stent comprises capturing elements (31) that offer stabilization of the endoprosthesis at the ventricular side and holding and capturing the native valve leaflets wide open.

In case the crown of this endoprosthesis is similar to embodiments 2 or 4a, the endoprosthesis is guided and navigated through the ventricle to capture/envelope the native mitral valve leaflets and then the rest of the endoprosthesis is expanded towards the atrium (embodiment 6a) (FIG. 7A).

In case the crown of this endoprosthesis is similar to embodiment 3 or 4b, the endoprosthesis is deployed from the atrium down to the lest ventricle, expanding the crown elements that trap the native mitral leaflets wide open and offer anchoring on the ventricular side of the annulus (embodiment 6b) (FIG. 7B).

The wire mesh incorporates a fabric or other material to make it instantly impermeable and may have a fabric skirt at the level of the annulus for better sealing. The stent part that is not covered by the mesh wire is skirted with a material so blocking any blood flow through its cells/struts. The endoprosthesis can have several standardized shapes and sizes. It can even be custom made based on measurements from the patient's anatomy obtained by medical imaging.

The prosthetic valve leaflets are attached to the stent of the endoprosthesis.

This endoprosthesis can be deployed either from its ventricular (embodiment 6a) or its atrial side (embodiment 6b).

Embodiment 7

Figure 8:
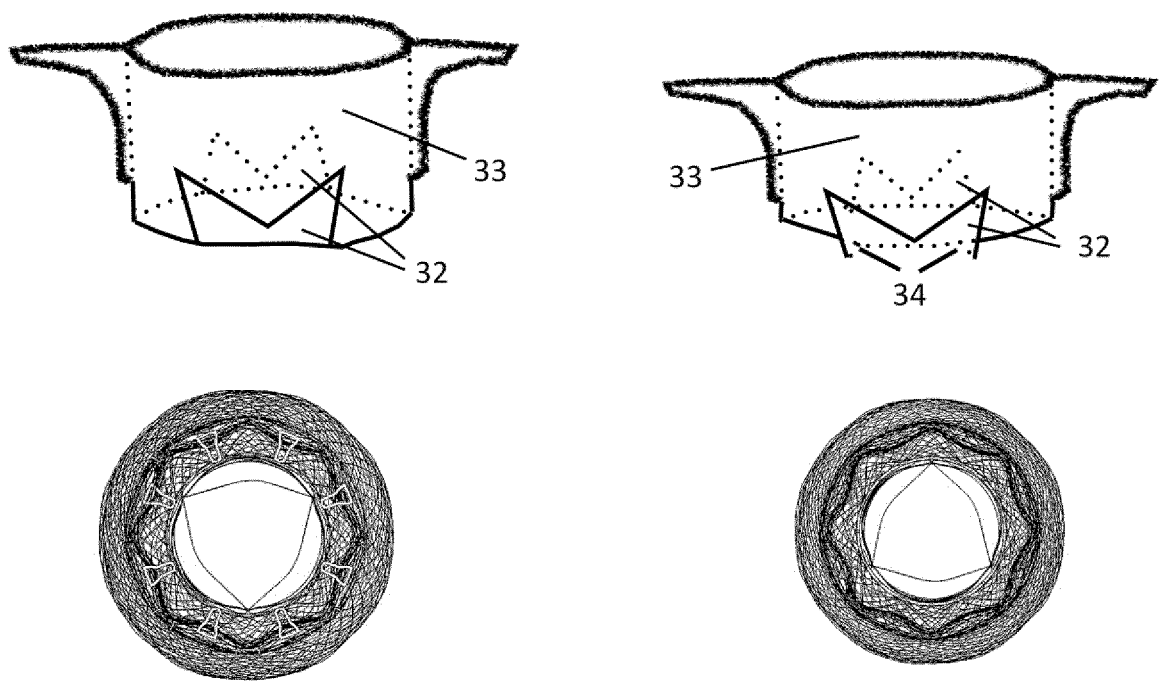
FIG. 8 shows another embodiment of a prosthetic valve according to the present invention.
Figure 9:
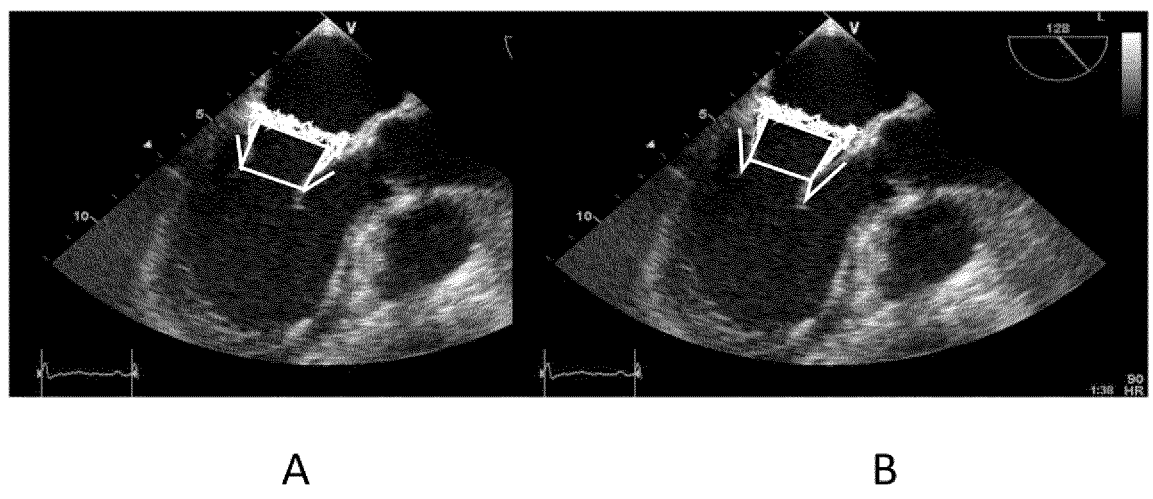
FIG. 9 shows the positioning of a prosthetic valve according to the present invention in a patient's heart.

This embodiment describes an endoprosthesis, which is a version of the embodiment 6 endoprosthesis. The main feature of this version that makes it distinct is that the interior capturing elements of the native mitral valve leaflets is the stent ring itself rather than parts of its crown (FIG. 8, FIG. 9A).

The crown of the stent comprising the exterior capturing elements (32) that provide navigational guidance for the positioning and the stabilization of the endoprosthesis at the ventricular side of the mitral valve annulus (first step of deployment). They expand outside of the native leaflets and as the endoprosthesis is pushed upwards and towards the annulus they are captured by these elements. Then, by continuing the delivery of the endoprosthesis the next part of it expanding is the stent ring itself (33) that apposes against the leaflets from their interior surface. When this occurs the native valve leaflets are captured between the stent and the its external capturing elements. Then the rest of the endoprosthesis is released. This has a thin wire mesh band expanding at the level of the annulus. The wire mesh then outexpands the annulus at its atrial side offering sealing and stabilization. The most ventricular end of the stent may be wire mesh-free (FIG. 8, FIG. 9B).

The endoprosthesis described is deployed from its ventricular side upwards and towards the atrium (embodiment 7a).

To avoid possible prolapse of the stent into the outflow of the left ventricle, a shorter part of the stent crown and its interior capturing elements (as described in endoprosthesis 6) may be preserved especially in the arc of the annulus that apposes towards the native anterior mitral leaflet (34).

In case the crown of this endoprosthesis is similar to embodiment 3, the endoprosthesis is deployed from the atrium down to the lest ventricle, expanding the crown elements that trap the native mitral leaflets wide open and offer anchoring on the ventricular side of the annulus (embodiment 7b).

The wire mesh incorporates a fabric or other material to make it instantly impermeable and may have a fabric skirt at the level of the annulus for better sealing. The stent part that is not covered by the mesh wire is skirted with a material so blocking any blood flow through its cells/struts.

The endoprosthesis can have several standardized shapes and sizes. It can even be custom made based on measurements from the patient's anatomy obtained by medical imaging.

The prosthetic valve leaflets are attached to the stent of the endoprosthesis.

This endoprosthesis can be deployed either from its ventricular side as described (embodiment 7a) or its atrial side (embodiment 7b).

The Delivery Catheter

1. Retrograde Access (Transventricular/Transapical)

Figure 10:
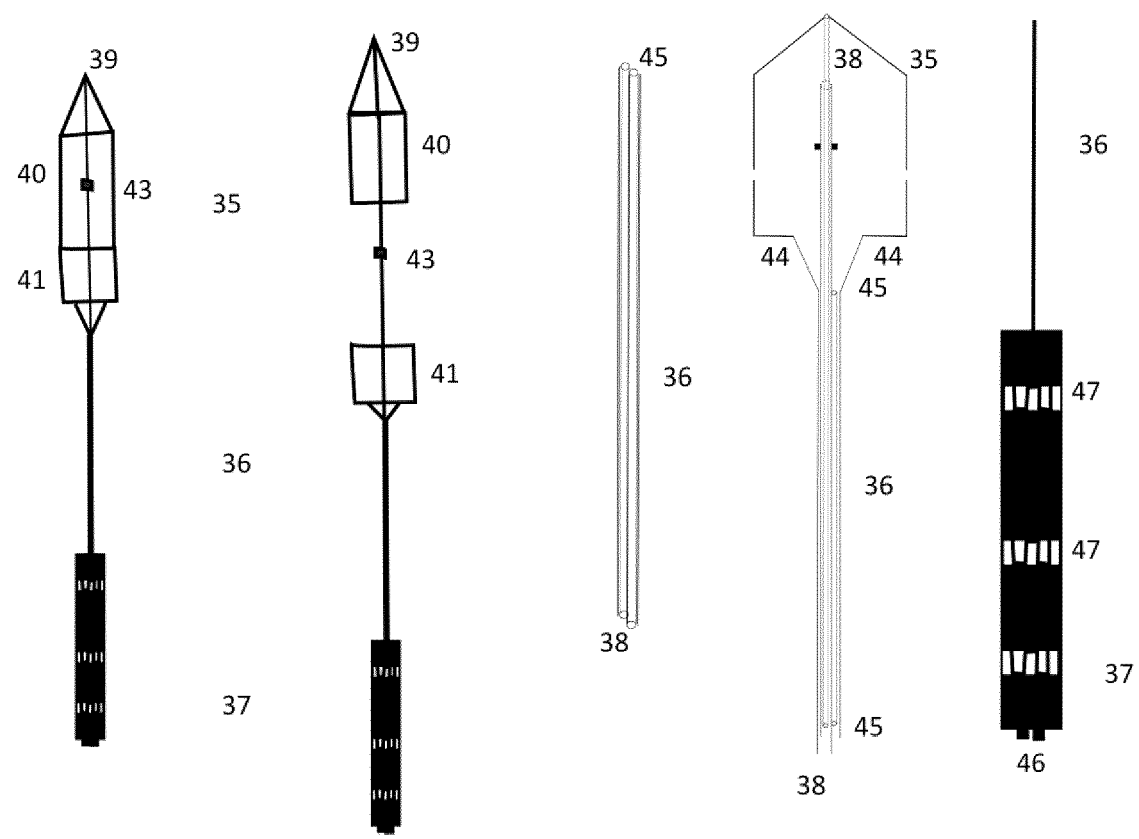
FIG. 10 shows an embodiment of a catheter for the delivery of a prosthetic valve according to the present invention.

The delivery catheter for the endoprosthesis of all embodiments consists of the capsule (FIG. 10,35) that contains the collapsed endoprosthesis, the shaft (36) and the handle (37). They all share a central lumen (38) that accommodates the guide wire over which the device is railed at the intended position of deployment.

The capsule contains the crimped endoprosthesis. Both of its ends are conical (39) to allow smooth tracking.

Figure 3:
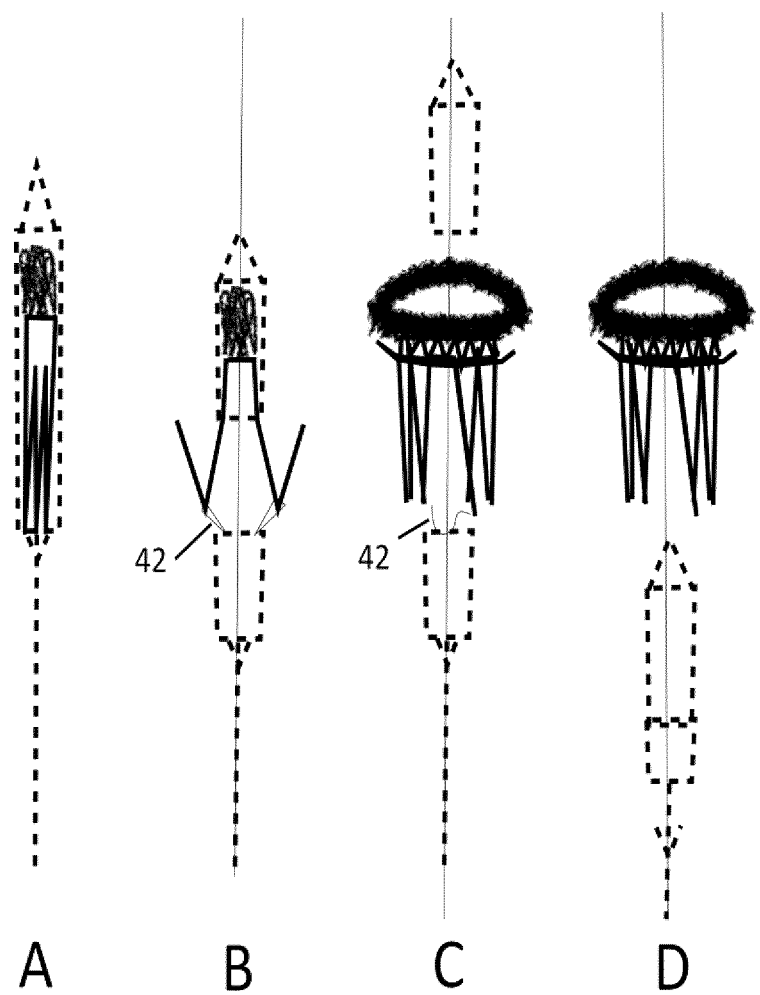
FIG. 3 shows one way of releasing a prosthetic valve according to the invention from its capsule.

For the endoprosthesis of the embodiments 1, 2 and 4a the capsule opens in two parts (FIG. 3, FIG. 10) the atrial part that is longer (40) and the ventricular part that is shorter (41). Each of these parts can move and open/close the respective part of the capsule independently. First the ventricular part is opened (withdrawn/pulled back) the part of the endoprosthesis crimped in this part expands (FIG. 3A, 3B), namely the outside capturing elements of the native valve leaflet expand fully, while their internal counterparts start to flare. When the external capturing/anchoring components are positioned deep behind the native leaflets and if possible in contact to the ventricular side of the annulus, the atrial part of the capsule is opened (advanced/pushed) releasing gradually first the internal native leaflet capturing elements, and then the stent ring and the wire mesh that appose to the annulus and towards the surrounding atrial wall (FIG. 3C, 3D).

When the endoprosthesis is fully deployed and functional it is still connected to the delivery catheter with a plurality of thin wires (such as ultra thin nitinol wires) (42), or screwing wires attached at the most ventricular edge of the stent (area connecting the external and internal capturing elements). Therefore complete atraumatic removal of the endoprosthesis is still feasible. When thin wires are used, they are threaded trough the stent. If the endoprosthesis position and function is satisfactory, one end of the thin wire is pulled till the entire thread is removed from the endoprosthesis and releases it. If the endoprosthesis needs to be removed both ends of the thin wires are pulled together. Another way of reversible connection of the thin wires to the stent is with Highwayman's knots, that allow tightening the knot and tugging by pulling one end of the wire, while the knot unties easily by pulling the other end of the wire.

Finally, an alternative way of attachment is by use of screwing wires that are fixed in female parts found at the stent end.

The part of the shaft traveling inside through the capsule has an inner hollow to accommodate the guide wire (38). The shaft of this lumen allows the push and opening of the atrial segment of the capsule. An additional shaft layer travels the capsule and the endoprosthesis is crimped on it. This layer has a plurality of pins at the level of the stent ring (43) on which the stent is passively stabilized by mirroring elements at its exterior surface.

The ventricular segment of the capsule is connected to an additional shaft layer (44) that is found on the delivery system (not in the capsule). A part of this layer starting at the capsule and having sufficient length can effortlessly expand to accommodate a part of the endoprosthesis in case it needs to be removed after complete deployment. This is required because the ventricular segment of the capsule is smaller and cannot accommodate the entire length of the collapsing stent and wire mesh. The entire length of the endoprosthesis needs to be sheathed in order the atrial capsule part to come close, meet and attach its ventricular part and the entire capsule safely removed.

When the delivery is considered successful and the holding wires are removed, the empty atrial capsule segment is withdrawn to meet and attach to the also empty ventricular capsule segment and then the capsule is closed and removed in one piece (FIG. 3D).

The shaft of the delivery system that connects the capsule to the handle has the previously described layers plus a space (could be in the form of an additional lumen) to accommodate the retracting holding wires of the endoprosthesis (45).

The handle is where all the above-described components of the shaft culminate. It has a central lumen for the guide wire to exit (46) and all the necessary knobs/dials/wheels (47) to facilitate the independent motions of the two capsule segments, and the thin wires that are used to resheath and remove the valve if needed. It is envisaged that one knob/dial/wheel is required for the movement of the atrial capsule, one for the movement of the ventricular capsule and possibly one for the pulling of the holding wires.

The delivery catheter is advanced in the left ventricle by itself or through a guide sheath. The guide sheath and/or the delivery catheter can have flexing capabilities to assist the coaxial and central to the annulus positioning of the capsule before and during delivery.

Considering the endoprostheses of the embodiments 3, 4b and 5 the delivery catheter is similar, but the capsule does not split into two parts, and it opens from its atrial tip towards the ventricle (the endoprosthesis of the embodiment 1 can also be released such a way) (FIG. 4B, 4C, 4D). First, the wire mesh is released completely within the atrium. The entire device then is pulled downward till the wire mesh seats firmly at the floor of the atrium. Then the capsule is further withdrawn releasing gradually the wire frame that apposes to the annulus and the crown components of the stent part in embodiments 3 and 4b or the ventricular part of the wire mesh in the embodiment 5.

The wire frame of the endoprosthesis and the course of the anchoring structures allow for complete retrieval of the endoprosthesis even after complete release.

The unnecessary parts of the delivery catheter for delivering this endoprosthesis are omitted (such as the separate shaft layer for the stabilization pins of the endoprosthesis and the handle wheel for moving the atrial segment of the capsule). A plurality of holding wires for retrieval of the endoprosthesis is reversibly attached (as described before) at the tips of the anchoring or other structures of the stent crown. By pulling these, the endoprosthesis reenters into the delivery capsule.

Figure 11:
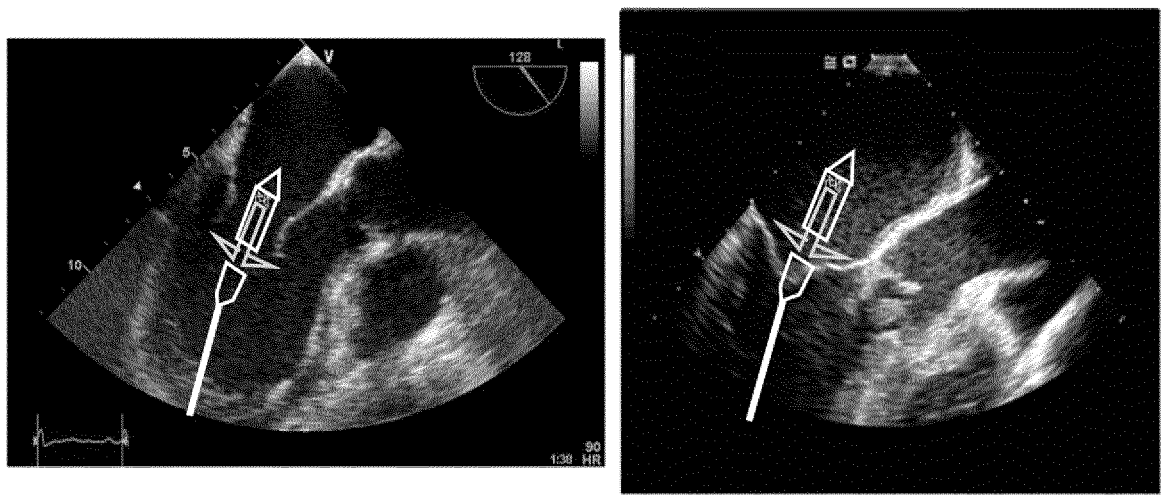
FIG. 11 shows the initial part of a transapical deployment of a prosthetic valve according to the present invention.
Figure 12:
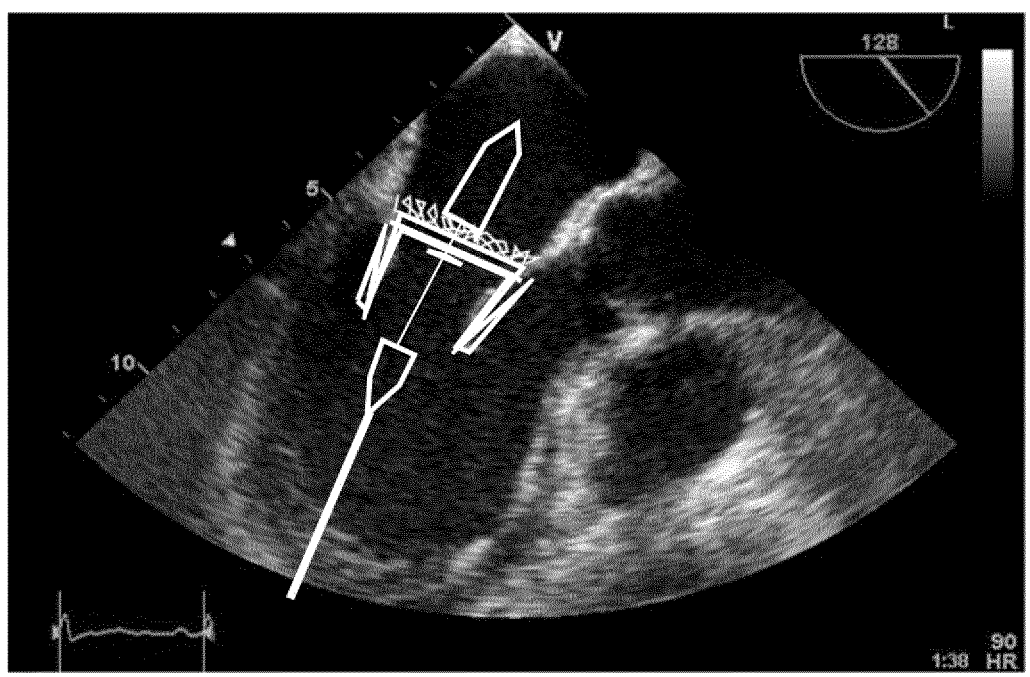
FIG. 12 shows a transapically deployed prosthetic valve according to the present invention.

FIGS. 11 and 12 illustrate an example of transapical delivery of one of the embodiments described.

2. Antegrade Access (Transeptal, or Direct Approach)

Figure 13:
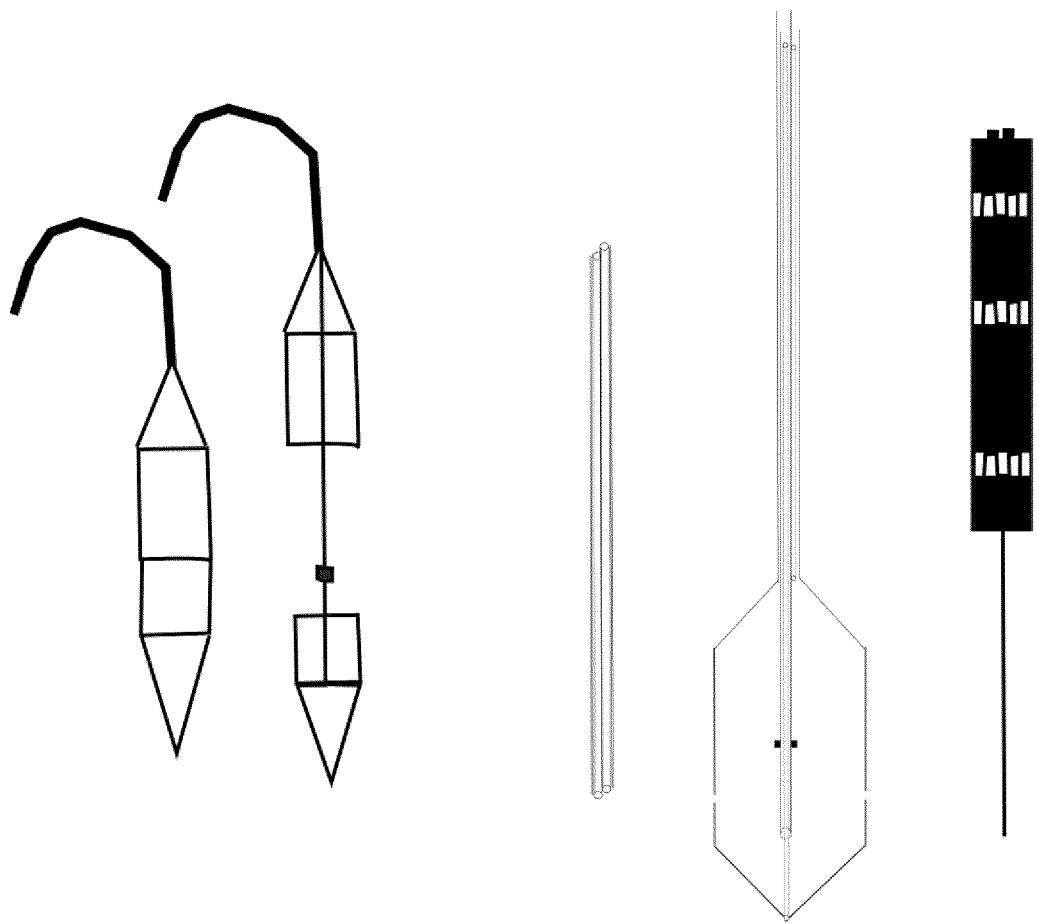
FIG. 13 shows a further embodiment of a catheter for the delivery of a prosthetic valve according to the present invention.

The delivery catheter for the endoprosthesis of all embodiments consists of the endoprosthesis capsule, the shaft and the handle (FIG. 13). They all share a central lumen that accommodates the guide wire over which the device is railed at the intended position of deployment.

The capsule contains the collapsed and crimped endoprosthesis. Its both ends are conical to allow smooth tracking forward and backward.

Figure 14:
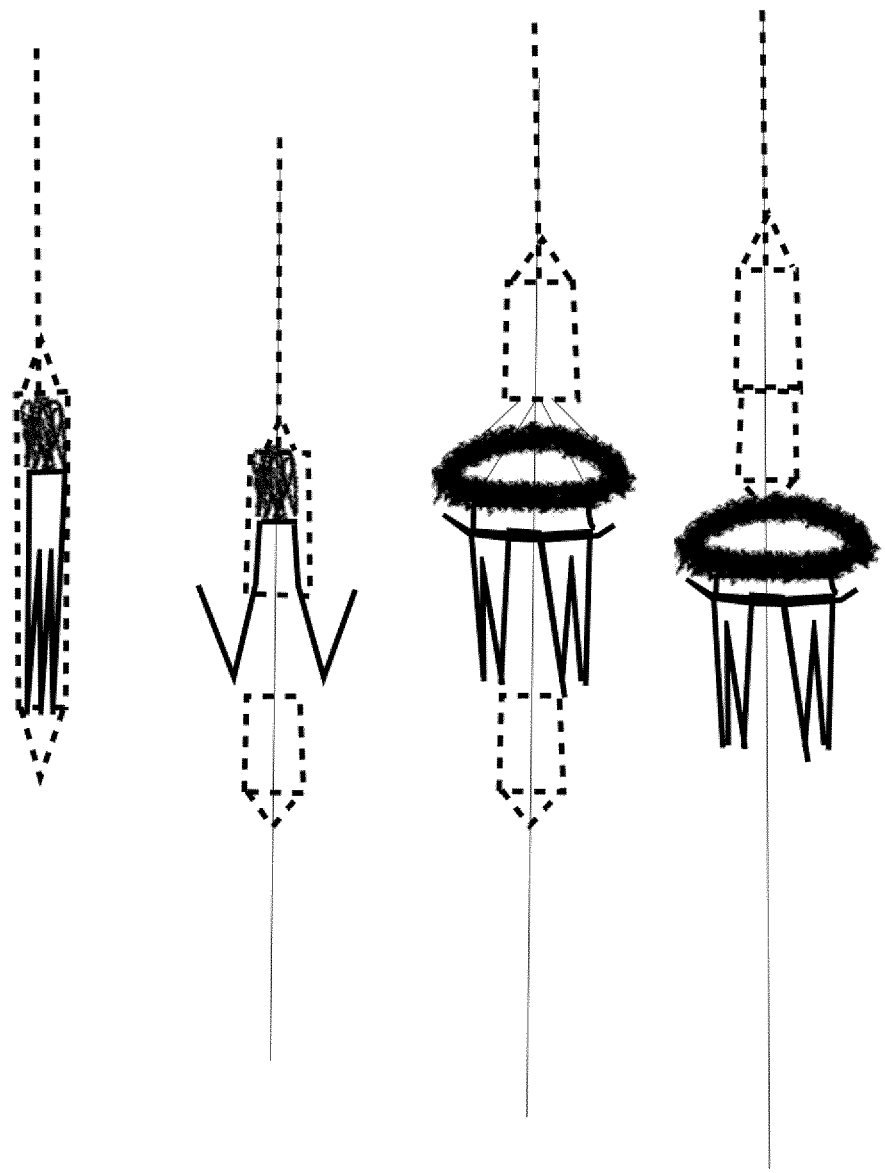
FIG. 14 shows one way of releasing a prosthetic valve according to the invention from its capsule.

For the endoprosthesis of the embodiments 1, 2 and 4a the capsule opens in two parts, the atrial part is longer and the ventricular part is shorter (FIG. 14). Each of these parts can move and open/close the respective part of the capsule independently. First the ventricular part is opened (advanced/pushed) and the part of the endoprosthesis crimped in this part expands, namely the external capturing elements of the native valve leaflets expand fully, while their internal counterparts start to flare. When the external capturing elements are positioned deep behind the native leaflets and in contact to the ventricular side of the annulus, the atrial part of the capsule is opened (withdrawn/pulled back) releasing gradually first the internal capturing elements of the stent crown, then the stent ring and finally the wired mesh. When the endoprosthesis is fully deployed and functional it is still connected to the delivery catheter with a plurality of thin wires (such as ultra thin nitinol wires) or screwing wires attached at the most atrial edges of the wire mesh. Therefore complete atraumatic removal of the endoprosthesis is still feasible. When thin wires are used, they are threaded trough suitable features of the wire mesh. If the endoprosthesis position and function is satisfactory, one end is pulled till the entire thread is removed from the endoprosthesis and releases it. If the endoprosthesis needs to be removed both ends of the nitinol wires are pulled, and it is gradually retracted into the atrial capsule. Another way of reversible connection of the thin wires to the mesh is with the Highwayman's knot that allows tightening the knot and tugging by pulling one end of the wire, while the knot unties easily by pulling the other end of the wire.

Finally, an alternative way of attachment is by use of screwing wires that are fixed in female parts in the mesh.

The part of the shaft traveling inside through the capsule has an inner lumen to accommodate the guide wire. The shaft of this lumen allows the push and opening of the ventricular segment of the capsule. An additional shaft layer travels the capsule and the endoprosthesis is crimped on it. This layer has a plurality of pins at the level of the stent ring on which the stent is passively stabilized by mirroring elements at its exterior surface.

The atrial segment of the capsule is connected to an additional shaft layer that is found on the delivery system (not in the capsule). This withdraws the atrial segment of the capsule, to completely release the endoprosthesis.

A part of this layer starting at the capsule and having sufficient length can effortlessly expand to accommodate a part of the endoprosthesis in case this needs to be removed after complete deployment. This is required because the entire length of the endoprosthesis needs to be sheathed into the atrial segment of the capsule. This additional space is required for the length of the stent that used to be accommodated into the ventricular capsule. The entire length of the endoprosthesis needs to be sheathed into the atrial capsule for the ventricular capsule segment to attach and close the capsule for safe removal.

If the deployment is not satisfactory, the wire mesh is first resheathed into the longer atrial capsule. The small part of the endoprosthesis that used to be accommodated into the ventricular capsule is also retracted into the atrial capsule, as described. When the delivery is considered successful and the holding wires are removed, the empty ventricular capsule segment is withdrawn to meet and attach to the also empty atrial capsule segment and they are then removed en block.

The shaft of the delivery system that connects the capsule to the handle has the previously described layers plus a space (could be in the form of an additional lumen) to accommodate the holding/retracting wires of the endoprosthesis.

The handle is where all the above-described components of the shaft culminate. It has a central lumen for the guiding wire to exit and all the necessary knobs/dials to facilitate the independent motions of the two capsule segments, and the wires that can be used to resheath and remove the valve if needed. It is envisaged that one knob/dial is required for the movement of the atrial capsule, one for the movement of the ventricular capsule and possibly one for the pulling of the holding wires.

The delivery catheter is advanced in the left atrium through a transeptal sheath or with direct access. The transeptal sheath and/or the delivery catheter can have flexing capabilities to assist the coaxial and central to the annulus positioning of the capsule before and during delivery.

Considering the endoprostheses of the embodiments 3, 4b and 5, the delivery catheter is similar, but the capsule does not split into two parts, and it opens from its atrial tip towards the ventricle (the endoprosthesis of the embodiment 1 can also be released such a way) (FIG. 4B, 4C, 4D). First, the wire mesh is released completely within the atrium by advancing the capsule towards the ventricle. The entire device then is pushed downward till the wire mesh seats firmly at the floor of the atrium. Then the capsule is further advanced releasing gradually the rest of the wire frame that apposes to the annulus and the crown components of the stent part in embodiments 3 and 4 or the ventricular part of the wire mesh in the embodiment 5.

The wire frame of the endoprosthesis and the course of the anchoring structures allow for complete retrieval of the endoprosthesis even after complete release.

A plurality of holding wires for retrieval of the endoprosthesis is reversibly attached (as described before) at the atrial edges of the wire mesh. By pulling these, the endoprosthesis reenters into the atrial segment of the delivery capsule.

Figure 15:
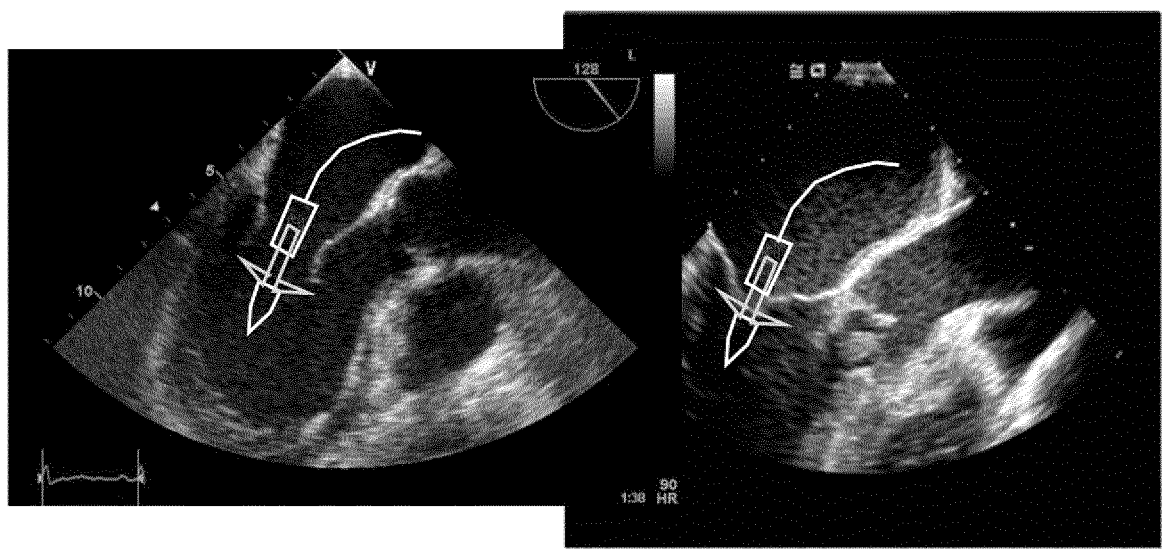
FIG. 15 shows the initial part of a transatrial/transeptal deployment of a prosthetic valve according to the present invention.
Figure 16:
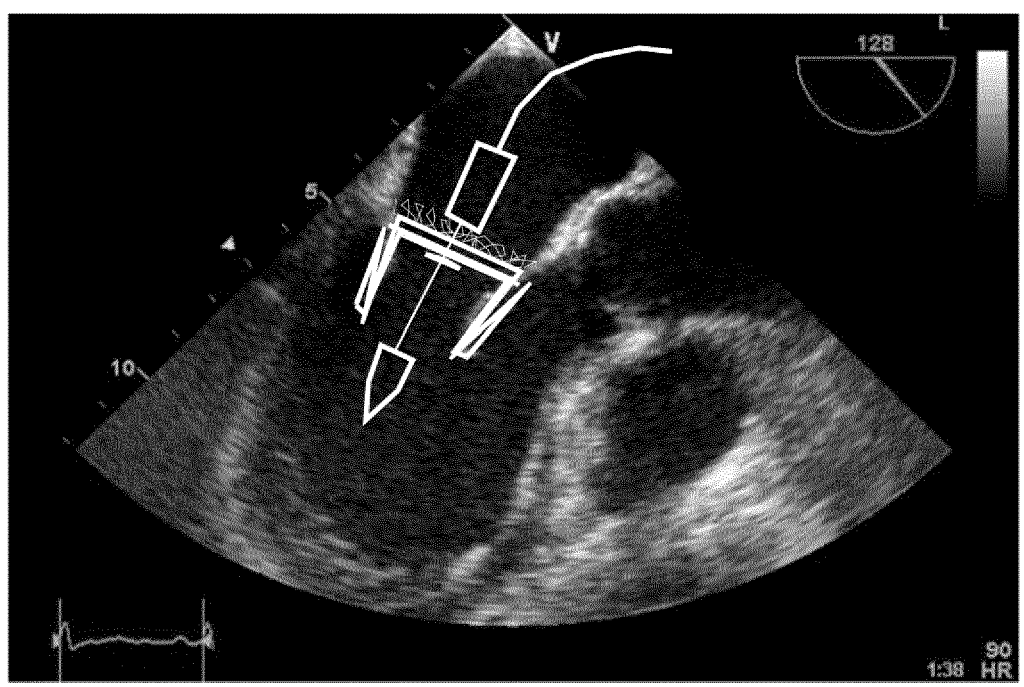
FIG. 16 shows a transatrially/transeptally deployed prosthetic valve according to the present invention.

FIGS. 15 and 16 illustrate an example of transapical delivery of one of the embodiments described.

In summary, the claimed inventions provide for all aspects of a successful transcatheter prosthetic mitral valve. They resolve the problems related to the uneven anatomy of the mitral valve by offering remedies at the level of the mitral valve leaflets (capture in a wide-open position and stabilization at the ventricular side), at the level of the annulus (optimal apposition, sealing and stabilization by the prosthetic valve frame) and at the level of the atrial floor (optimal apposition, sealing and stabilization by the prosthetic valve frame).

These are achieved with: 1. A refined combination of two components in the frame of the endoprosthesis, namely the wire stent contributing optimal radial strength for the formation of the frame lumen and the orifice of the prosthetic valve and the wire mesh contributing plasticity and optimal conformation. 2. An innovative method to capture and immobilize the native valve leaflets and navigationally guides the deployment of the prosthetic valve offering tactile feedback and at the same time the much-required stabilization at the ventricular level.

The invention claimed is:

1. A prosthetic mitral valve for transcatheter delivery comprising:
   a collapsible and self-expandable interior stent having an atrial end and a ventricular end, the interior stent having a sealing skirt and defining a lumen supporting a plurality of valve leaflets; and
   a collapsible and self-expandable exterior wire mesh surrounding the interior stent, the exterior wire mesh extending along substantially an entire length of the interior stent, the exterior wire mesh having a lower radial strength than the interior stent for conforming to a native mitral valve, the exterior wire mesh attached at least to at the atrial end and forming a body around the stent, the exterior wire mesh having a first portion with an enlarged diameter sized for placement above a mitral annulus for sealing and stabilizing the prosthetic mitral valve on an atrial side, the exterior wire mesh having a second portion with a reduced diameter for contacting the mitral annulus and for extending to a ventricular side of the mitral annulus;
   wherein the stent forms at its ventricular end a plurality of native leaflet capturing elements, the capturing elements extending in a ventricular direction beyond a ventricular end of the exterior wire mesh and then turning in an atrial direction such that the capturing elements are positioned radially outwardly from the exterior wire mesh, the capturing elements adapted for trapping native mitral leaflets against the wire mesh and for anchoring the prosthetic mitral valve on a ventricular side.

2. The prosthetic mitral valve according to claim 1, wherein the wire mesh extends longitudinally towards the ventricular end of the stent forming a body around the stent.

3. The prosthetic mitral valve according to claim 2, wherein the wire mesh reaches the ventricular end of the stent.

4. The prosthetic mitral valve according to claim 2, wherein the wire mesh extends beyond the ventricular end of the stent.

5. The prosthetic mitral valve according to claim 1, wherein sizes of the native leaflet capturing elements vary between them.

6. The prosthetic mitral valve according to claim 1, wherein shapes of the native leaflet capturing elements vary between them.

7. The prosthetic mitral valve according to claim 1, wherein the wire mesh comprises a sealing material.

8. The prosthetic mitral valve according to claim 7, wherein the sealing material is a fabric.

9. The prosthetic mitral valve according to claim 1, wherein the wire mesh comprises at its outer surface barbs or spikes.

10. The prosthetic mitral valve according to claim 1, wherein the stent is made of collapsible nitinol, or stainless steel.

11. The prosthetic mitral valve according to claim 1, wherein the wire mesh is made of collapsible nitinol or stainless steel.

12. A catheter for delivery of the prosthetic mitral valve according to claim 1, further comprising a capsule, a shaft and a handle.

* * * * *